(12) United States Patent
Canty et al.

(10) Patent No.: US 9,239,275 B2
(45) Date of Patent: Jan. 19, 2016

(54) DIRECT LINE SAMPLING AND DILUTION SYSTEM

(71) Applicant: J.M. Canty Inc., Buffalo, NY (US)

(72) Inventors: Thomas M. Canty, Amherst, NY (US); Paul J. O'Brien, East Aurora, NY (US); Justin R. Hallbach, Clarence, NY (US)

(73) Assignee: J.M. CANTY INC., Buffalo, NY (US)

( * ) Notice: Subject to any disclaimer, the term of this patent is extended or adjusted under 35 U.S.C. 154(b) by 379 days.

(21) Appl. No.: 13/789,750

(22) Filed: Mar. 8, 2013

(65) Prior Publication Data

US 2014/0250987 A1 Sep. 11, 2014

(51) Int. Cl.
*G01N 1/38* (2006.01)
*G01N 1/20* (2006.01)
G01N 15/00 (2006.01)
G01N 1/10 (2006.01)

(52) U.S. Cl.
CPC .. *G01N 1/38* (2013.01); *G01N 1/20* (2013.01); G01N 15/00 (2013.01); G01N 2001/1025 (2013.01); G01N 2001/2057 (2013.01); G01N 2015/0053 (2013.01)

(58) Field of Classification Search
CPC ......... G01N 1/10; G01N 1/2035; G01N 1/38; G01N 2001/205; G01N 2001/2057
USPC ................... 73/61.68, 64.56, 863.71–863.73
See application file for complete search history.

(56) References Cited

U.S. PATENT DOCUMENTS

| 4,562,748 A * | 1/1986 | Mrochek et al. ........... 73/863.73 |
| 4,804,519 A * | 2/1989 | Sainz et al. ..................... 422/81 |
| 5,007,297 A * | 4/1991 | Sommer ...................... 73/865.5 |
| 6,357,306 B1 * | 3/2002 | Jaeger ......................... 73/863.83 |
| 6,359,742 B1 | 3/2002 | Canty et al. |
| 2003/0174306 A1* | 9/2003 | Grant et al. ..................... 356/36 |
| 2012/0291568 A1* | 11/2012 | Gransæther ................ 73/864.63 |

* cited by examiner

*Primary Examiner* — Hezron E Williams
*Assistant Examiner* — David Z Huang
(74) *Attorney, Agent, or Firm* — Leydig, Voit & Mayer, Ltd.

(57) ABSTRACT

A direct line sampling system includes a flow line for a process flow, a diluent flush line for a diluent, and a sampling valve structure disposed in the flow line. The sampling valve structure includes a sampling chamber and has a first position in which the sampling chamber is in communication with the flow line so as to provide a path for the process flow through the sampling chamber. The sampling chamber captures a sample from the process flow when the sampling valve structure switches to a second position in which the sampling chamber is in communication with the diluent flush line. The diluent flushes the sample to a mixing chamber disposed downstream of the diluent flush line where the sample is diluted. An outlet line extends from an outlet of the mixing chamber to an analysis instrument configured to analyze particles in the diluted sample of the process flow.

16 Claims, 6 Drawing Sheets

DIRECT LINE SAMPLING AND DILUTION SYSTEM

FIELD

The present invention relates to a particle analysis method, particularly a method suitable for the chemical and petrochemical industries where there is a desire to accurately sample, dilute and analyze dense slurries of fluid at the fluid line in order to provide improved process control information in near real time.

BACKGROUND

Representative sampling and dilution is advantageous when using instruments to analyze a process flow in order to accurately study the process fluid or slurry. A dense slurry can prevent signals, such as laser, visual, infrared or ultraviolet light, from penetrating the mass of particles. As a result, a corresponding sensor is unable to receive the signals in order to analyze the particulate features including, for example, size, shape and quantity. By diluting a representative sample of the process flow, the signals can penetrate the fluid or slurry and accurate signals can be obtained and analyzed. If the sample is representative, the analysis will present an accurate characterization of the process flow as a whole. Being able to dilute the fluid or slurry at the flow line allows the process flow to be analyzed in a timely manner. If the sample removed and taken to a lab for analysis, the process requires considerable manpower and time, both of which are disadvantage. Moreover, the time required for lab analysis typically prevents the possibility of obtaining real time results. Due to the delay in performing lab analysis, the characteristics of the process flow can change considerably before the analysis is known. is critical in analyzing a process in a timely manner. During this time, if unfavorable conditions exist, it is possible for the process to proceed to an out of control condition.

Many flow analysis systems use a sample from a single point in the process flow. However, such point sampling can lead to several errors. First, due to the possible stratification of the flow in the line, the point sample is unlikely to be an accurate representation of the flow. This is particularly true for slurries, where the weight to lift ratios of the particulates can result in varying characteristics of the flow across the line due to gravity. Further, the piping configuration itself can cause the flow to stratify so that the point sample is unlikely to be representative of the entire flow. In addition, the types of samplers used to provide a point sample of the process flow often exacerbate the problems associated with stratification of the flow. The structure of the sampler within the flow line may lead to changes in the fluid velocity within the flow, which will lead to further stratification of the flow. Lastly, the sampling tube devices that are often used for point samples can change the velocity of the sampled fluid which also leads to stratification and may cause heavier particles to drop out of the sampled flow and be excluded from the sample entirely. This iso-kinetic characteristic of a drawn sample is always of concern when trying to achieve a representative sample.

SUMMARY

An aspect of the present invention is to provide a system for direct line sampling and analysis that uses dilution and provides accurate analysis of a representative sample of the process flow being analyzed.

In an embodiment, the present invention provides a direct line sampling system including a flow line for a process flow including particles therein, a diluent flush line for a diluent and a sampling valve structure disposed in the flow line. The sampling valve structure includes a sampling chamber with a substantially fixed volume and has a first position in which the chamber is in communication with the flow line so as to provide a path for the process flow through the chamber and so as to capture a sample from the process flow when the sampling valve structure switches to a second position in which the chamber is in communication with the diluent flush line in which the sample of the process flow is flushed from the chamber. A mixing chamber is disposed downstream of the diluent flush line and is configured to mix the sample with the diluent so as to dilute the sample. An outlet line extends in a first direction from an outlet port of the mixing chamber. An analysis instrument is disposed in the outlet line and configured to analyze particles in the diluted sample of the process flow. A diluent control line with an outlet supply port is disposed in a vicinity of the outlet line upstream of the analysis instrument and is configured to supply diluent in a direction opposite the first direction of the outlet line so as to regulate the flow of the particles through the outlet line and to the analysis instrument.

In an other embodiment, the present invention provides a direct line sampling system including a flow line for a process flow that has a first cross sectional area, a diluent flush line for a diluent and a sampling valve structure disposed in the flow line. The sampling valve structure includes a sampling chamber having a substantially fixed volume and a second cross sectional area that is equal to the first cross sectional area. The sampling valve structure has a first position in which the sampling chamber is in communication with the flow line so as to provide a path for the process flow through the sampling chamber and so as to capture a sample from the process flow when the sampling valve structure switches to a second position in which the sampling chamber is in communication with the diluent flush line so as to flush the sample of the process flow from the sampling chamber. A mixing chamber is disposed downstream of the diluent flush line and configured to mix the sample with the diluent so as to dilute the sample. An outlet line extends from an outlet of the mixing chamber. An analysis instrument is disposed in the outlet line and configured to analyze particles in the diluted sample of the process flow.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following.

DETAILED DESCRIPTION

Figure 1:
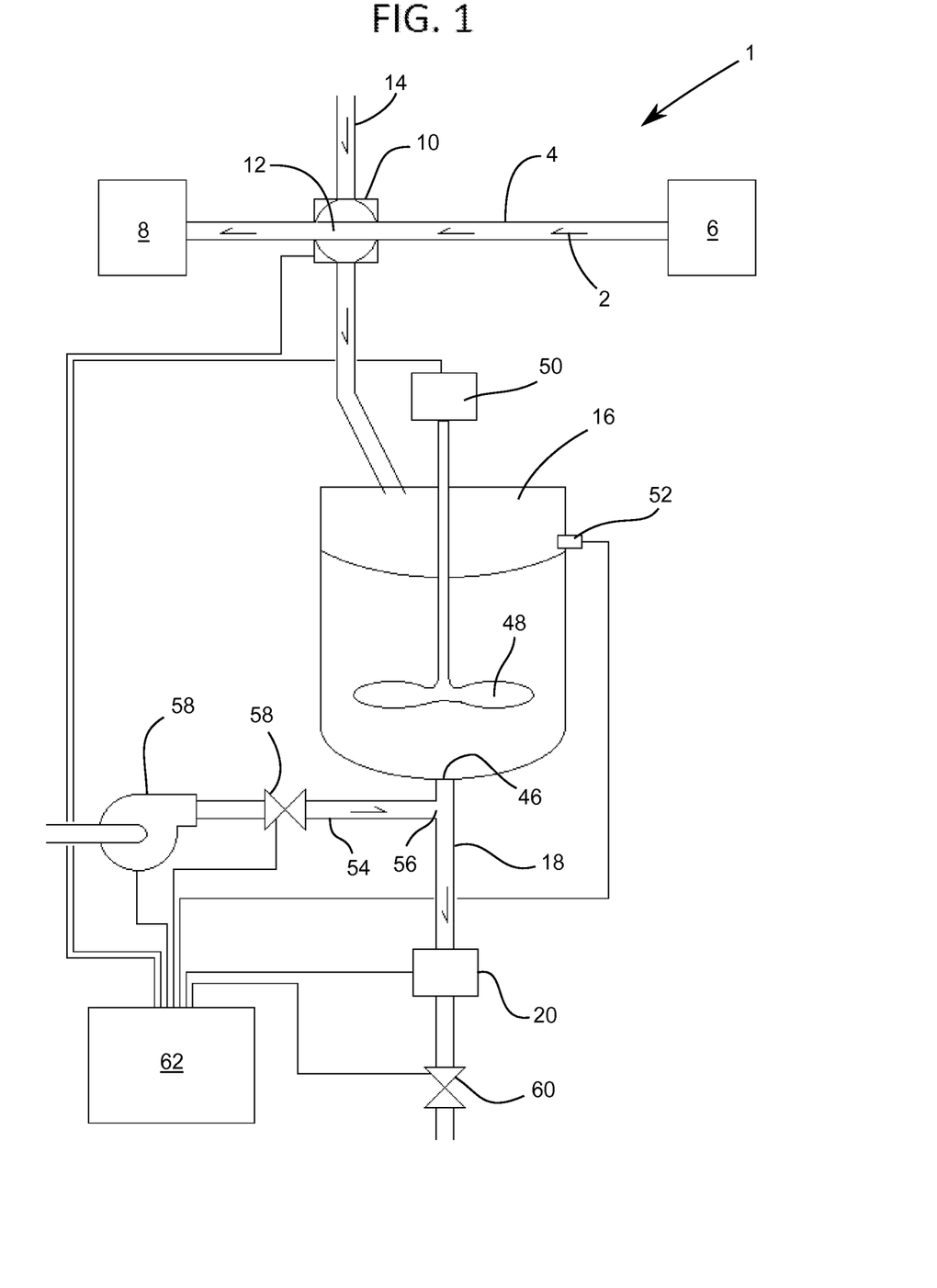
FIG. 1 shows a direct line sampling system in accordance with an embodiment of the present invention.

FIG. 1 shows a direct line sampling system 1 in accordance with an embodiment of the present invention. The system captures a sample from a process flow 2 flowing in a line 4 from a first process station 6 to a second process station 8. The flow line 4 can be a pipe, duct or other conduit configured to carry the process flow from the first process station 6 to the second 8. Each of the process stations 6, 8 can be any of a number of stations in the flow of a process including apparatuses for collecting or treating the flow, such as a drill hole, a tank, a hydrosizer, a reservoir, the surrounding environment, a filter, a grinding machine, a separator, a slurry tank, a de oiler, an injection pump, or a shaker screen. For example, in an oil drilling process, the first process station 6 may be a drill hole of an oil well, and the second process station 8 may be a mud reservoir. In another example, in a strip mining operation, the first process station 6 may be a field slurry tank and the second process station may be a hydrosizer. In yet another example, relating to oil refining, the first process station 6 may be a separation tank and the second process station 8 may be the surrounding environment.

A sampling valve structure 10 is disposed in the flow line 4 and is configured to separate a sample volume from the flow for analyzing the characteristics of the flow. The sampling valve structure 10 includes a sampling chamber 12 in communication with the flow line 4 such that the process flow passes through the chamber 12. To separate the sample from the flow, the sampling valve structure 10 is switched to a second position in which the sampling chamber 12 is disconnected from the flow line and coupled to a diluent flush line 14. Once separated from the bulk of the flow, the sample is flushed from the sampling chamber 12 by diluent through the diluent flush line 14 to a mixing chamber 16 where it is mixed with the diluent to form a diluted sample. From the mixing chamber 16, the diluted sample proceeds through an outlet line 18 to an analysis instrument 20, where it is analyzed. In the exemplary embodiment, the process flow is a slurry and the dispersed particles in the diluted sample are counted and analyzed with respect to their weight, volume, abundance and other characteristics.

Figure 2:
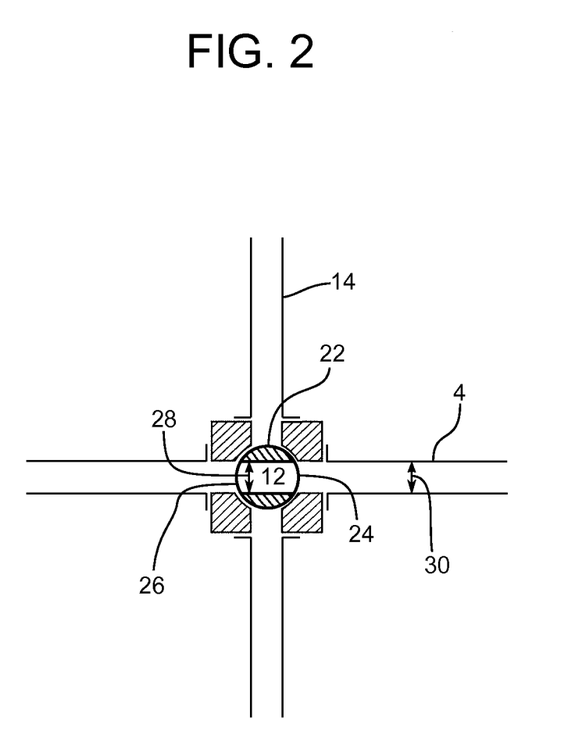
FIG. 2 shows an embodiment of a valve structure in accordance with the invention.

FIG. 2 schematically illustrates an example of the operation of the sampling valve structure 10 in an embodiment using a movable valve component 22 with an inlet port 24, an outlet port 26 and the sampling chamber 12 extending therebetween. Thus, the sampling chamber 12 can be a valve port disposed within the movable valve component 22. As an example, the illustrated valve component 22 is part of a 4-way straight port ball valve, where the valve component 22 is the ball of the valve. When the valve component 22 is in a first position, as shown in FIG. 2, the inlet 24 and outlet 26 are connected to the flow line 4, such that the process flow 2 is able to flow through the sampling chamber 12 unimpeded. When a sample is to be taken, the valve 22 component is switched to a second position so as to disconnect the inlet 24 and outlet 26 of the valve component 22 from the flow line 4 and connect the valve component 22 to the diluent flush line 14. As the valve component 22 is switched from the first to the second positions, the contents of the process flow within the sampling chamber 12 are captured and can be used as the sample. Once the valve component 22 has switched to the second position, the sampling chamber 12 is connected to the diluent flush line 14 by ports 24, 26 so that the sample can be flushed from the sampling valve structure 10 to the mixing chamber 16.

In a preferred embodiment, the valve component 22 is part of a full port valve as illustrated in FIG. 2, such that the port defining the chamber 12 of the valve component 22 has a diameter that is substantially the same as the diameter of the process flow line 4. As a result, the cross sectional area of a flow path through the sampling valve structure 10 is the same as the cross sectional area of the flow line 4 itself. This similarity between the flow areas of the process flow line 4 and the sampling valve structure 10 prevents the sampling valve structure 10 from impeding the process flow 2 as it passes therethrough when the structure 10 is in the first position and coupled to the flow line 4. Moreover, because the sampling valve structure 10 provides a flow path that replicates the flow path through the flow line 4, the sample captured by the valve structure 10 is an accurate representation of the entire flow through the flow line. Thus, the sampling valve structure 10 shown in FIG. 2 has certain advantages over a point sample, which could be subject to inaccuracies resulting from stratification of the process flow around the associated sampling structure.

In a preferred embodiment, the flow line 4 is a main line in a process, carrying the entire process flow in the associated system. In other words, the flow line 4 is not a by-pass branch that extends off of a larger conduit. Thus, as shown in FIG. 1, the flow line 4 carries the entire process flow 2 from the first process station 6 to the second process station 8. When the sampling valve structure 10 is in the first position, all of the process flow 2 proceeding from the first process station 6 passes through the valve structure 10. To accommodate the flow, the valve structure 10 is configured so that the volumetric flow rate through the valve structure 10 is the same as the volumetric flow rate entering the flow line 4 from the first process station 6.

Figure 3:
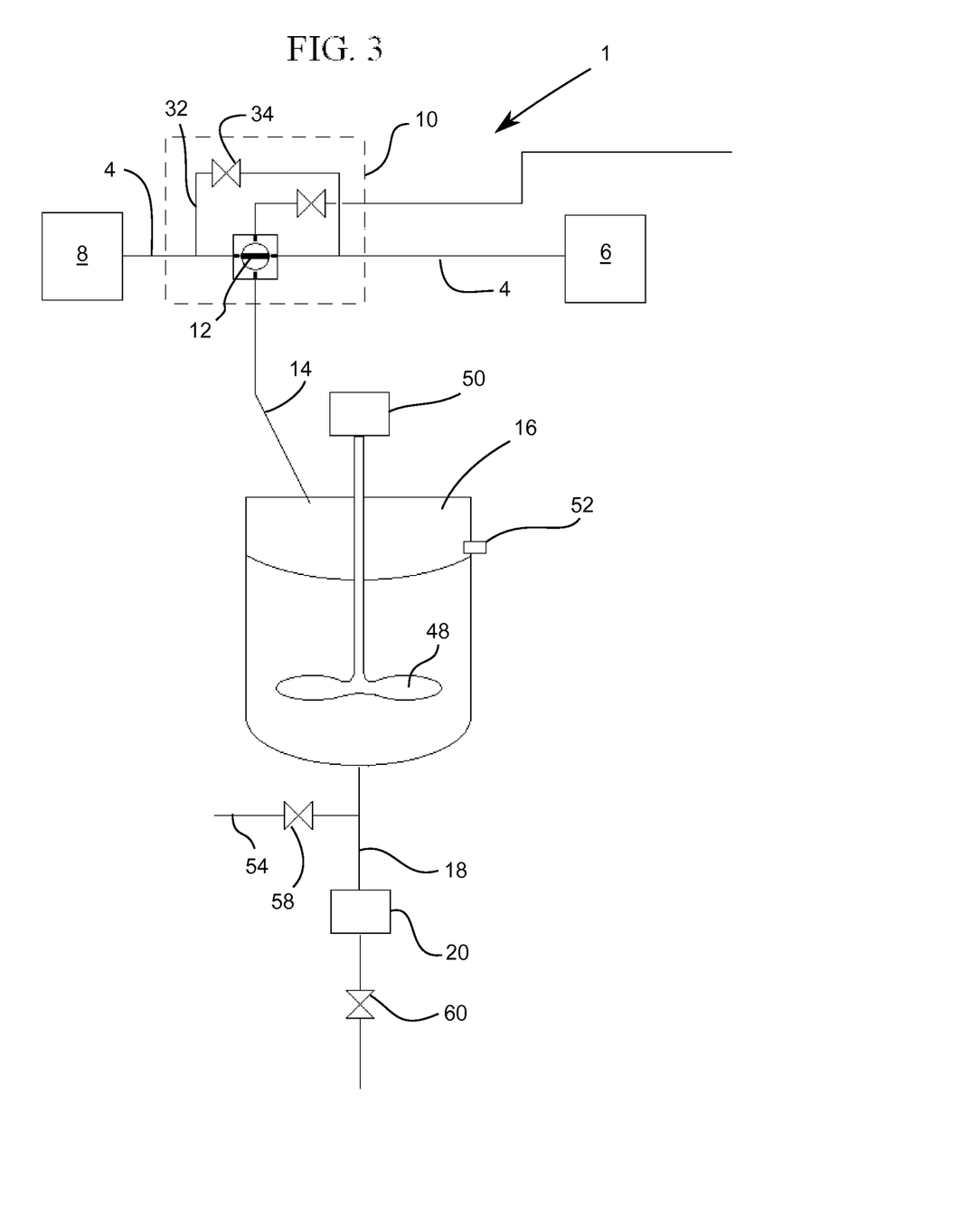
FIG. 3 shows an embodiment of the sampling system including a diversion line.

In order to keep the process flow moving, the sampling valve structure 10 can include a diversion path 32, as shown in FIG. 3, that allows the process flow 2 to pass through the sampling valve structure 10 while the captured sample in the sampling chamber 12 is flushed into the mixing chamber 16 through the diluent flush line 14. The diversion path 32 thereby enables the process to continue with little interruption while the sample is captured. Preferably, the diversion path 32 is only open when the sampling chamber 12 is coupled to the diluent flush line 14. To achieve this operation, a diversion valve port 34 can be disposed in the diversion path 32 and operable to be closed when the valve structure 10 is in the first position and open when the valve structure is in the second position. Thus, the diversion valve port 34 of the diversion path 32 preferably operates synchronously with the operation of the sampling chamber 12. As shown in FIG. 3, this can be achieved by including the diversion valve port 34 of the diversion path 32 in the single valve package with the sampling chamber 12. Alternatively, the diversion valve port 34 can be disposed in a separate valve. In such a case, the synchronization of the valve in the diversion path 32 with the sampling chamber 12 could be achieved by a controller configured to operate the respective valves, or could be achieved by manual synchronized operation of the valves.

As a further alternative to the single valve package shown in FIG. 3, the sampling valve structure 10 can include several discrete valves that operate cooperatively. For example, in the embodiment shown in FIG. 4, the sampling chamber 12 is provided by a pipe section disposed between a pair of three-port valves, 40, 42. When the sampling valve structure 10 is in the first position, the three-port valves 40, 42 are configured so that both ends of the pipe defining the sampling chamber 12 are in communication with the flow line 4. In contrast, when the sampling valve structure 10 is in the second position, the valves 40, 42 are arranged so that the sampling chamber 12 is in communication with the diluent flush line 14. A further valve 44 can be disposed in an diversion line 32 branching off the flow line 4 upstream of the first three port valve 40 and rejoining the flow line 4 downstream of the second three port valve 42. To operate this sampling valve structure as a single entity, the valves 40, 42, 44 can be actuated by signals from an electronic controller, described in more detail below. An advantage of using a group of valves to provide the sampling valve structure 10 is that the sampling chamber 12 can be provided by a length of pipe or conduit. This allows the volume of the sampling chamber 12 to be chosen as desired, based on the length of pipe used for the sampling chamber, without being constrained by the diameter of the flow line 4.

Once the sampling valve structure is in the second position and the sampling chamber 12 is coupled to the diluent flush line 14, the sample is flushed out of the chamber 12 by a diluent and carried to the mixing chamber 16. The amount of diluent used to flush the sampling chamber 12 can be freely selected as desired. For example, a relatively small amount of diluent can be used to flush the majority of the captured sample into the mixing chamber 16, or a sustained flow of diluent can be used to clean the sampling chamber 12 until the analysis unit 20 is unable to identify any of the sample in the diluted fluid. Preferably, the diluent is selected to be miscible with the sample. For example, if the process flow 2 is oil based, the diluent can also be oil based. Alternatively, if the process flow is water-based, a water-based diluent may be used. Once the diluent is no longer being flushed through the sampling chamber 12, the sampling valve structure 10 can be returned to the first position so that the process flow can once again proceed through the structure 10.

The captured sample is carried with diluent to the mixing chamber 16 where it is further diluted. In a preferred embodiment, as shown in the drawings, the mixing chamber 16 is a tank that is configured to hold a variable amount of fluid. Thus, the very top of the tank is configured to typically be empty. In a preferred embodiment, the top of the tank is operated at atmospheric pressure and may be open to the atmosphere. The mixing tank 16 includes an outlet 46 that leads to the outlet line 18. In the illustrated embodiment, the outlet 46 is disposed in the bottom of the tank 16 so that gravity can provide the pressure needed to drive the diluted sample through the outlet line 18. In a preferred embodiment, the outlet 46 associated with outlet line 18 is the only outlet from the mixing chamber 16. As shown in FIG. 1, the outlet 46 may indeed be the only opening into or out of the bottom of the mixing tank 16, or even the lower half of the mixing tank 16.

The mixing chamber 16 may include a mixing device 48 for aiding in the dilution of the sample in the diluent. The mixing device 48 may be a physical agitator, as shown in FIG. 1, that is driven by a motor 50 and includes paddles for mixing the fluid in the chamber 16. Alternatively, the mixing device 48 can be a magnetic agitator. The sample can also be mixed with the diluent in the mixing chamber 16 by other methods, such as by using sonic waves.

In a preferred embodiment, the mixing chamber 16 includes a fill sensor 52 that provides a measurement of the fill level of the fluid held in the mixing chamber 16. The fill sensor 52 can include one or more binary detectors that sense the presence or absence of the fluid at a particular level. Alternatively, the fill sensor 52 may be configured for continuous level sensing using, for example, a pressure sensor or an ultrasonic transmitter. In operation, the fill sensor 52 can be used to maintain the mixing chamber at a predetermined level, or within predetermined upper and lower thresholds.

The diluted sample flows from the mixing chamber 16 through the outlet line 18 to the analysis instrument 20, where it is analyzed. To carefully analyze the contents of the sample, it is preferable to pass the sample through the instrument 20 in a highly diluted state, so that the contents of the sample do not arrive at the analysis instrument 20 simultaneously, which would likely lead to inaccurate analysis. For example, in the exemplary embodiment, the process flow is a slurry including particles suspended in a fluid, and the analysis instrument 20 is configured to analyze certain characteristics of the particles. However, maintaining the particles in the dilution can be problematic, especially when the particles are heavy and/or the viscosity of the fluid is comparatively small. For example, mixing sand particles in water can be difficult with regard to maintaining a suspension. If the particles fall through the suspension they can enter the analysis instrument in a collection that is too dense for the instrument to properly analyze, resulting in an error in the measurement. In order to address this problem, the line sampling system shown in FIG. 1 includes a diluent control line 54 that is configured to add diluent to the system at a location that is in a vicinity of the outlet line 18. The addition of the diluent from the diluent control line 54 provides a flow in the opposite direction of the analysis instrument through a portion of outlet line 18, which prevents the particles from reaching the analysis instrument all at once. In the embodiment shown in FIG. 1, the lift force provided by the diluent from the diluent control line 54 keeps the particles suspended for longer periods of time before they flow to the analysis instrument 20. The extent to which the particles are kept suspended in the outlet line 18 or in the mixing tank 16 is controllable by varying the flow of diluent in the diluent control line 54. So long as the pressure at the outlet supply port 56 of the diluent control line 54 is greater than the pressure at the bottom of the mixing tank 16, the control diluent will flow upwards keeping the particles suspended.

In the embodiment shown in FIG. 1, the diluent control line 54 has an outlet supply port 56 that opens into the outlet line 18. However, it is also possible for the outlet supply port 56 of the diluent control line 54 to open into the bottom of the mixing tank 16. For example, one or more ports could be provided in proximity of the mixing tank outlet 46 and configured to direct the flow of control diluent upwards to keep the particles suspended and limit their entrance into the outlet line.

The flow of diluent through the diluent control line 54 can be regulated by metering device 58 disposed in the control line 54. The metering device 58 can be a valve, a pump, or a combination thereof, as shown in FIG. 1. The flow through the analysis instrument 20 can also be regulating by controlling the flow through the outlet line 18 itself. This can be achieved using a flow control device 60 disposed in the outlet line. The flow control device 60 can be, for example, a valve or an orifice. In a preferred embodiment, the flow control device 60 is positioned downstream of the analysis instrument 20.

Operation of the metering device 58 in the diluent control line 54 and, if applicable, the flow control device 60 disposed in the outlet line 18 can each be carried out manually by an operator of the line sampling system. Alternatively, the flow characteristics can be regulated by a controller 62 that sends control signals to the metering device 58 and/or the flow control device 60. In a further embodiment, each of the described components of the system can be operated by the controller 62. Moreover, the controller 62 can also receive data from the fill sensor 52 or other sensor that monitor the operation of the system. The term "sensor" is meant to be used in its broadest sense to include one or more sensors and related components that may be associated with the system 1 and that may cooperate to sense various functions, conditions, operations, and operating characteristics of the machine.

The controller 62 may be an electronic controller that operates in a logical fashion to perform operations, execute control algorithms, store and retrieve data and other desired operations. The controller 62 may include or access memory, secondary storage devices, processors, and any other components for running an application. The memory and secondary storage devices may be in the form of read-only memory (ROM) or random access memory (RAM) or integrated circuitry that is accessible by the controller. Various other circuits may be associated with the controller such as power supply circuitry, signal conditioning circuitry, driver circuitry, and other types of circuitry.

The controller 62 may be a single controller or may include more than one controller disposed to control various functions and/or features of the line sampling system. The term "controller" is meant to be used in its broadest sense to include one or more controllers and/or microprocessors that may be associated with the system 1 and that may cooperate in controlling various functions and operations of the system. The functionality of the controller 62 may be implemented in hardware and/or software without regard to the functionality. The controller 62 may rely on one or more data sets relating to the operating conditions of the system, for example, the flow characteristics, that may be stored in the memory of controller. Each of these data sets may include a collection of data in the form of tables, graphs, and/or equations.

Figure 5:
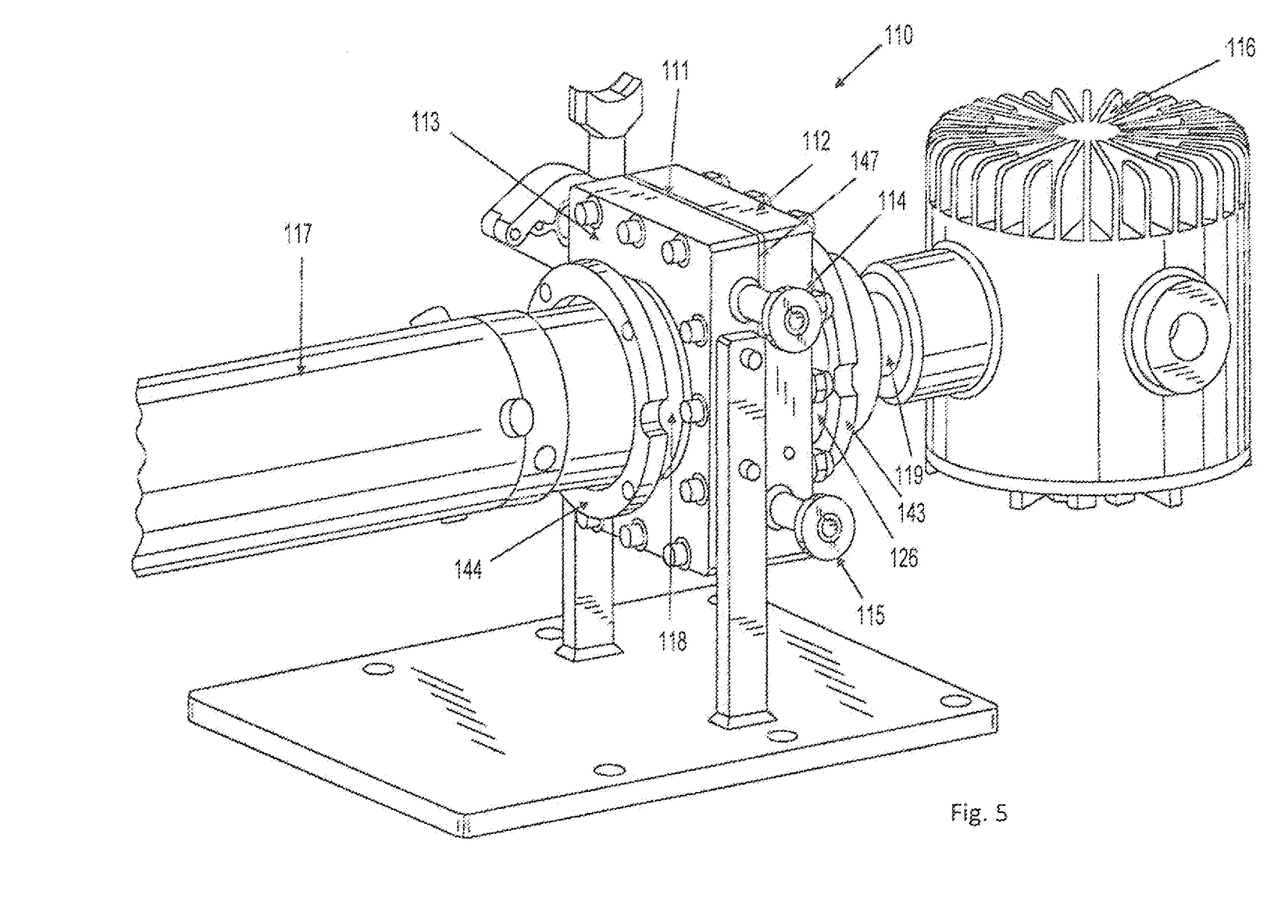
FIG. 5 shows a perspective view of an embodiment of an analysis instrument.
Figure 6:
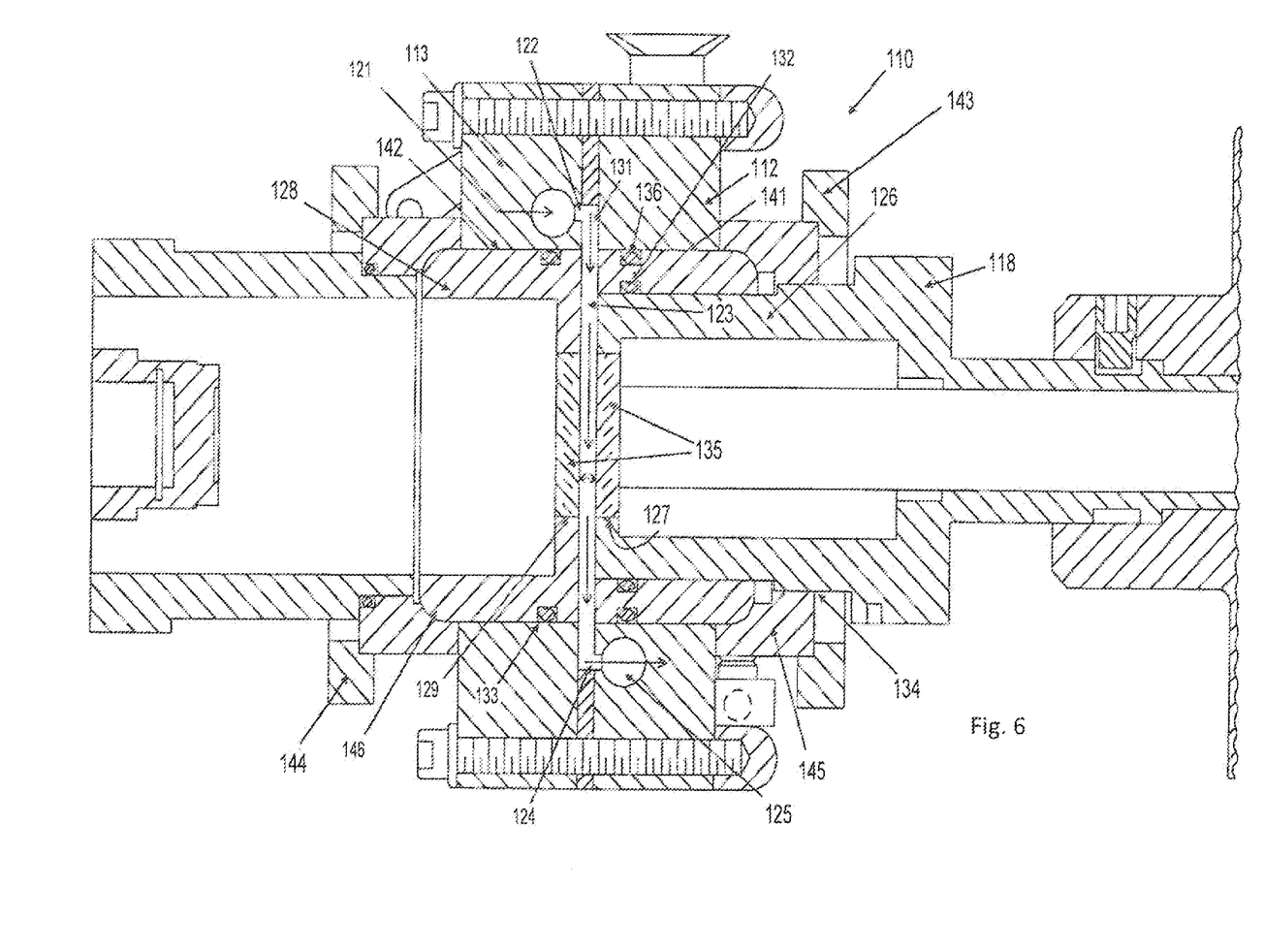
FIG. 6 shows a cross-sectional view of the analysis instrument in FIG. 5.

FIGS. 5 and 6 shows an embodiment of an analysis instrument 20 configured to analyze the diluted sample flowing through outlet line 18. The exemplary analysis instrument is in the form of a flow cell device 110 including a housing 111, which consists of a first housing half 112 joined together with a second housing half 13. A gasket 147 may be disposed between the two housing halves so as to form a housing gap 131 between the first and second housing halves. Second housing half 113 includes an inlet conduit 14 which is in fluid communication with the housing gap 131 between the two housing halves. Likewise, first housing half 112 includes an outlet conduit 115 which is in fluid communication with the housing gap 131 between the two housing halves. Viewing assembly 118 is coupled to the housing 111 and includes a first viewing member 126 and a second viewing member 128, which are disposed opposite one another so as to form adjustable an aperture 123 therebetween. It is also possible for the viewing assembly to include a single viewing member adjustable with respect to the housing and forming an adjustable aperture between the viewing member in the housing. In the illustrated embodiment, the aperture 123 is formed between viewing members 126 and 128 and is in fluid communication with housing gap 131. However, unlike the housing gap 131, the aperture 123 is adjustable while the fluid is flowing through the flow cell device, by moving the first viewing member 126 with respect to the housing 111.

Inlet conduit 114 is attached, for example using a hose or high pressure pipeline, to an upstream side of the outlet line 18. Likewise, the outlet conduit 115 is attached, for example using a hose or high pressure pipeline, to a downstream side of the outlet line 18.

A light source 116 may be coupled to the first viewing member 126 in order to illuminate the fluid as it flows in the aperture 123. Viewing and illumination can also take place through the same port. The light source 116 includes a light pipe 119, which, in this embodiment, contains fiber optic bundles that carry the light to the first viewing member 126. The light source includes an incandescent bulb emitting visible white light. However, a variety of light sources may be used emitting light from across the visible and non-visible spectrum to illuminate the fluid in the aperture. The light source may include any of a number of sources for emitting the light including, for example, various types of light bulbs, lasers, light emitting diodes, reflection of ambient light, and light emitting chemical reactions.

As shown in FIG. 6, after passing through the inlet conduit 114, the diluted sample enters an inlet reservoir 121 which is formed in an interior portion of the second housing half 113. From the inlet reservoir, the fluid passes through inlet 122 into the housing gap 131 between the first and second housing halves 112, 113. From the housing gap 131, the fluid passes through an aperture 123 defined, in this embodiment, as the space between first viewing member 126 and second viewing member 128. In the embodiment shown in the figures, the viewing assembly 118 includes first and second viewing members 126, 128. The viewing assembly 118 is coupled to first housing half 112 at a first viewing assembly opening 141 in housing half 12. The viewing assembly 118 includes a first adapter element 145 which is coupled to the first housing half 112 with the help of a first flange 143, which may be bolted to the first housing half 112. A first scaling element 136 is disposed between a first adapter member 145 of the viewing assembly 118 and housing half 12 so that fluid may not escape through the opening 141. A second sealing element 132 is disposed between the first viewing-member 126 and the first adapter member 145. The viewing assembly 118 is also coupled to the second housing half 113 at the second viewing assembly opening 142 in housing half 13. The viewing assembly 118 includes a second adapter member 146, which is secured to housing half 113 with the help of a second flange 144, which may be bolted to the second housing half 13. A third sealing element 133 is disposed between the second adapter member 146 of the viewing assembly 118 and housing half 113 so that fluid may not escape through the opening 42.

As shown in FIG. 5, the light source 116 is coupled to the first viewing member 127 to illuminate the fluid in the aperture 23 and a camera 117 is coupled to second viewing member 128. Thus, in the illustrated embodiment, the viewing is performed using the camera 117. Camera 117 may be any kind of camera, such as, for example, a still camera, a video camera, or a CCD camera, and may transmit the image to a remote location, where it can be observed, for example on a video monitor. The image may also be sent as an electronic file to a microprocessor, where various measurements, analysis and calculations are made to the image information. A person of ordinary skill in the art would recognize that viewing could be performed with or without instrumentation such as a camera from either or both viewing elements. Similarly, illumination of the fluid could be performed, through either or both of the viewing elements, or with no special lighting apparatus, such as allowing ambient light to shine through one or both of the viewing members. Though both members 126 and 128 are referred to as viewing members, it is not necessary that both members enable a viewing of the fluid. In the preferred embodiment, viewing member 128 enables a viewing of the fluid through camera 117, and viewing member 126 enables an illumination of the fluid using light source 116. It is also not necessary that the two viewing members enable either viewing or illumination. For example, one viewing member may be made of solid steel and enable neither, such that viewing and/or viewing and illumination are carried out through the other viewing member.

In the illustrated embodiment, the first and second viewing members 126, 128 each define viewing ports 127 and 129 respectively. Disposed within each viewing port is a transparent glass window 135 to allow illumination and or viewing of the fluid in the aperture 123. The surface of each window toward the aperture is preferably flush with a surface of the respective viewing member 126, 128. The glass windows 135 are preferably fused directly to an annular metal frame, for example as described in U.S. Pat. No. 6,359,742. Thus, the glass windows 135 can be fused directly to a metal end portion of the respective viewing member 126, 128, shaped to form an annular frame. Preferably the construction is sturdy enough to handle fluids having high pressures, such as pressures of up to 6000 p.s.i. The sturdy fused glass to metal construction enables a wide field of view for a broader view of the flow stream and thus better analytical accuracy, and a larger flow cell to process more fluid in less time. The sturdy construction also enables the device to be employed in rugged field environments, such as when vibration and other ambient effects are present that might cause a thin glass window flow cell to leak or break.

In an embodiment, the present invention also relates to a method of using the line sampling system to analyze a sample from a process line at the line. An exemplary embodiment of the method is described herein with reference to the system illustrated in FIG. 1. However, the method may be used with the other described sampling systems above, or other variations of a line sampling system.

Figure 4:
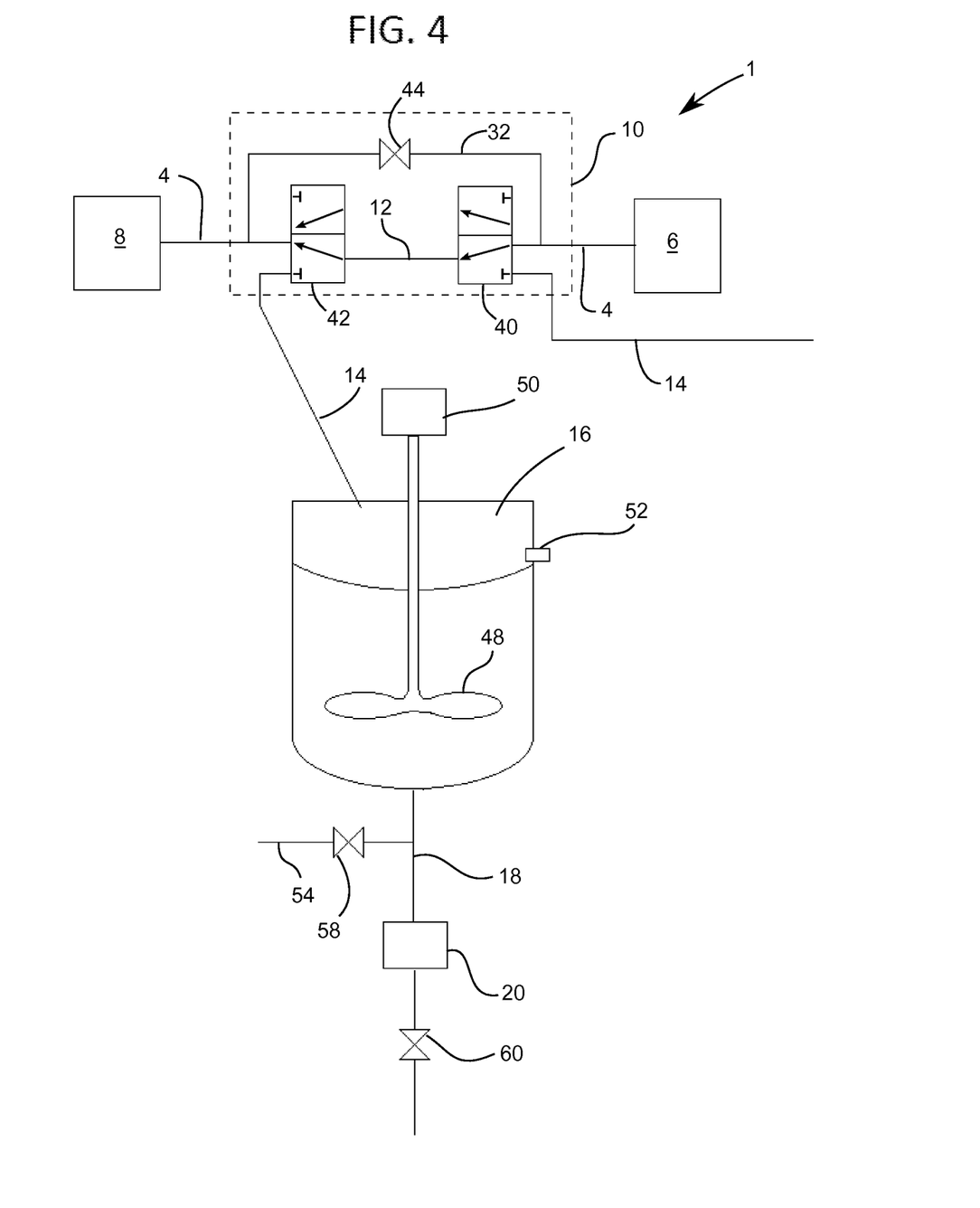
FIG. 4 shows an embodiment of a sampling system including a valve structure formed by various valves.

A process flow 2 is directed from a first process station 6 to a second process station 8 through the flow line 4 and a sampling chamber 12 disposed in the flow line 4. In this embodiment, the process flow 2 is a dense slurry including a substantial quantity of particles. To capture a sample of the process flow 2, the sampling valve structure 10 disposed in the flow line 4 is switched from the original position, in which the sampling chamber 12 is in communication with the flow line 4, to a second position. The volume of the process slurry that is disposed within the sampling chamber 12 before it is moved out of the original position is thereby captured by the sampling chamber 12 and provides an accurate sample of the process flow 2 flowing through the line 4. In connection with the movement of the sampling chamber 12 from the original position to the second position, a diversion line can be opened to allow the process flow to continue flowing from the first process station 6 to the second process station 8 (as shown in FIGS. 3 and 4).

Once the sampling valve structure 10 is switched to the second position, the sampling chamber 12 comes into fluid communication with the diluent flush line 14. A diluent is then run through the sampling chamber 12 and the sample of the process flow is washed into a mixing chamber 16. Within the mixing chamber 16, the sample is diluted and mixed with the diluent by the mixing device 48. As the particles from the sample fall toward the outlet drain 46 leading to the outlet line 18, additional diluent is added to the mixing tank 16 through the diluent control line 54. This additional diluent flows up through the outlet line 18 into the mixing tank 16, providing a lifting force on the particles that counters gravity. Thus, by regulating the flow through diluent control line 54, the velocity of the particles in the sample can be controlled so that the analysis instrument 20 does not receive too many particles all at once. Control of the flow through the diluent control line 54 is carried out by operating the metering device 58 disposed in the diluent control line 54. As stated previously, the metering device may include, for example, a valve, a pump, or both, as shown in FIG. 1. In a preferred embodiment, the metering device 58 is operated to maintain the fill level in the mixing tank 16 to a defined volume as indicated by the fill sensor 52.

The flow of fluid through the analysis instrument 20 can also be regulated using a flow control device 60 disposed in the outlet line 18. Thus, the flow control device 60 has an influence on the velocity of the dilution and the particles suspended therein as they flow through the analysis instrument 20.

Operation of the system can be managed by the controller 62, which sends control signals to the various operating components of the system, such as the components of the sampling valve structure 10, the motor 50 of the mixing device 48, the metering device 58 of the diluent control line 54, the flow control device 60 and the analysis instrument. The controller 62 can also receive signals from various sensors, including the fill sensor 52 and the analysis instrument 20.

As the particles in the dilution begin to pass through the analysis instrument 20, software associated with the instrument will begin to register an increase in the particulate presence in the fluid and start a capture and analysis procedure. The diluent can be continuously provided to the mixing chamber during the analysis to maintain a minimum level of fluid in the mixing chamber 16 and to maintain an optimal flow of particulate through the analysis instrument 20. As a portion of the sample of slurry flows from the mixing chamber 16 through the outlet line 18, the dilution of the sample will rise and the analysis instrument will detect a decline in the particle count. Once the analysis instrument identifies that a base level of particle flow has been reached, the analysis of the sample can be discontinued. If desired, the diluent may continue to flow through the diluent control line 54 or the diluent flush line 14 to clean any remnants of the sample from the mixing chamber 16 and outlet line 18. The system is then ready to capture and analyze another sample of the process flow 2. Depending on the value of the process flow, the components of the sample can be collected after leaving the analysis instrument. The diluent can also be filtered and recycled for further use, if desired.

While the invention has been particularly shown and described with reference to preferred embodiments thereof, it will be understood by those skilled in the art that various changes in form and details may be made therein without departing from the spirit and scope of the invention.

What is claimed is:

1. A direct line sampling system comprising:
a flow line for a process flow including particles therein;
a diluent flush line for a diluent;
a sampling valve structure disposed in the flow line and including a sampling chamber with a substantially fixed volume, the sampling valve structure having a first position in which the sampling chamber is in communication with the flow line so as to provide a path for the process flow through the sampling chamber and so as to capture a sample from the process flow when the sampling valve structure switches to a second position in which the chamber is in communication with the diluent flush line so as to flush the sample of the process flow from the chamber;
a mixing chamber disposed downstream of the diluent flush line and configured to mix the sample with the diluent so as to dilute the sample;
an outlet line extending in a first direction from an outlet port of the mixing chamber;

an analysis instrument disposed in the outlet line and configured to analyze particles in the diluted sample of the process flow; and a diluent control line including an outlet supply port disposed in fluid communication with the outlet line upstream of the analysis instrument and configured to supply diluent in a direction opposite the first direction of the outlet line so as to regulate the flow of the particles through the outlet line and to the analysis instrument.

2. The sampling system recited in claim 1, wherein the outlet supply port of the diluent control line opens into the outlet line so as to supply diluent directly to the outlet line and into the mixing chamber.

3. The sampling system recited in claim 1, wherein the outlet supply port of the diluent control line opens into the mixing chamber.

4. The sampling system recited in claim 1, wherein the mixing chamber is a mixing tank and the outlet line is gravity fed.

5. The sampling system recited in claim 1, further comprising a metering device disposed in the diluent control line; and
a controller coupled to the metering device and operable to send control signals to the metering device so as to control a rate of flow of diluent through the diluent control line in order to regulate the flow of the particles through the outlet line and to the analysis instrument.

6. The sampling system recited in claim 5, wherein the mixing chamber is a mixing tank including a fill-level sensor, wherein a flow through the outlet line is due to gravity, and wherein the controller is coupled to the fill-level sensor so as to receive sensor signals from the fill-level sensor, and is operable to adjust the control signals sent to the metering device based on the sensor signals received from the fill-level sensor.

7. The sampling system recited in claim 1, further comprising a flow control device disposed in the outlet line downstream of the outlet supply port of the diluent control line, and
a controller coupled to the flow control device and operable to send control signals to the flow control valve so as to control a rate of flow of the diluted sample through the outlet line in order to regulate the flow of particles through the outlet line and to the analysis instrument.

8. A direct line sampling system comprising:
a flow line for a process flow, the flow line having a first cross sectional area;
a diluent flush line for a diluent;
a sampling valve structure disposed in the flow line and including a ball valve comprising a sampling chamber having a substantially fixed volume and a second cross sectional area that is equal to the first cross sectional area, the sampling valve structure having a first position in which the sampling chamber is in communication with the flow line so as to provide a path for the process flow through the sampling chamber and so as to capture a sample from the process flow when the sampling valve structure switches to a second position in which the sampling chamber is in communication with the diluent flush line so as to flush the sample of the process flow from the sampling chamber;
a mixing chamber disposed downstream of the diluent flush line and configured to mix the sample with the diluent so as to dilute the sample;
an outlet line extending from an outlet of the mixing chamber; and
an analysis instrument disposed in the outlet line and configured to analyze particles in the diluted sample of the process flow.

9. The sampling system recited in claim 8, wherein the ball valve of the sampling valve structure is a full port valve comprising a valve component with an inlet and an outlet and including the sampling chamber between the inlet and outlet, wherein the inlet and outlet of the valve component are in communication with the flow line when the sampling valve structure is in the first position, and wherein the inlet and outlet of the valve component are in communication with the diluent flush line when the sampling valve structure is in the second position.

10. The sampling system recited in claim 8, wherein the sampling valve structure includes a diversion path in communication with the flow line when the sampling valve structure is in the second position so as to provide a path for the process flow to continue flowing through the sampling valve structure when the sampling valve structure is in the second position.

11. The sampling system recited in claim 8, wherein the analysis instrument is configured for visual analysis of the diluted sample.

12. A method for analyzing a sample from a process flow at the process flow line, the method comprising:
providing a process flow including particles therein through a flow line;
providing a sampling valve structure in the flow line, the sampling valve structure including a sampling chamber and being switchable between a first position in which the sampling chamber is in fluid communication with the flow line so as to provide a path for the process flow through the sampling chamber and a second position in which the sampling chamber is in fluid communication with a diluent flush line that leads to a mixing chamber;
switching the sampling valve structure from the first position to the second position so as to capture a sample of the process flow by breaking the fluid communication between the sampling chamber and the flow line, and flush the sample of the process flow from the sampling chamber to the mixing chamber using a diluent from the diluent flush line;
diluting the sample with the diluent in the mixing chamber so as to provide a diluted sample;
draining the diluted sample from the mixing chamber through an outlet line that extends from the mixing chamber in a first direction, the outlet line including an analysis instrument disposed therein;
providing a diluent control line including an outlet supply port disposed in fluid communication with the outlet line upstream of the analysis instrument;
supplying a further diluent in a direction opposite the first direction of the outlet line so as to provide a lift force on particles within the diluted sample in order to regulate the flow of the particles through the outlet line and to the analysis instrument; and
analyzing the particles of the diluted sample as they pass through the analysis instrument.

13. The method recited in claim 12, wherein the outlet supply port of the diluent control line opens into the outlet line and the diluent is supplied directly to the outlet line.

14. The method recited in claim 12, wherein the diluent is supplied to the outlet line at a pressure sufficient to flow into the mixing chamber.

15. The method recited in claim 12, wherein the mixing chamber is a mixing tank and the diluted sample is drained by the force of gravity.

16. The method recited in claim 12, wherein the supplying diluent is regulated so as to maintain a minimum volume of diluted sample in the mixing chamber.

* * * * *